(12) United States Patent
Subramaniam et al.

(10) Patent No.: US 9,586,923 B2
(45) Date of Patent: Mar. 7, 2017

(54) SPRAY OXIDATION PROCESS FOR PRODUCING 2,5-FURANDICARBOXYLIC ACID FROM HYDROXYMETHYLFURFURAL

(75) Inventors: Bala Subramaniam, Lawrence, KS (US); Xiaobin Zuo, Lawrence, KS (US); Daryle H. Busch, Lawrence, KS (US); Padmesh Venkitasubramanian, Forsyth, IL (US)

(73) Assignees: University of Kansas, Lawrence, KS (US); Archer Daniels Midland Company, Decatur, IL (US)

( * ) Notice: Subject to any disclaimer, the term of this patent is extended or adjusted under 35 U.S.C. 154(b) by 0 days.

(21) Appl. No.: 14/239,819

(22) PCT Filed: Aug. 28, 2012

(86) PCT No.: PCT/US2012/052600
§ 371 (c)(1),
(2), (4) Date: Apr. 29, 2014

(87) PCT Pub. No.: WO2013/033058
PCT Pub. Date: Mar. 7, 2013

(65) Prior Publication Data
US 2015/0183755 A1 Jul. 2, 2015

Related U.S. Application Data

(60) Provisional application No. 61/529,425, filed on Aug. 31, 2011.

(51) Int. Cl.
| | | |
|---|---|---|
| *C07D 307/68* | (2006.01) |
| *B01J 2/02* | (2006.01) |
| *B01J 27/128* | (2006.01) |
| *B01J 19/10* | (2006.01) |
| *B01J 19/24* | (2006.01) |
| *B01J 4/00* | (2006.01) |
| *C07D 307/46* | (2006.01) |
| *B01J 31/04* | (2006.01) |

(52) U.S. Cl.
CPC ............ *C07D 307/68* (2013.01); *B01J 2/02* (2013.01); *B01J 4/002* (2013.01); *B01J 19/10* (2013.01); *B01J 19/24* (2013.01); *B01J 27/128* (2013.01); *B01J 31/04* (2013.01); *C07D 307/46* (2013.01); *B01J 2219/00006* (2013.01); *B01J 2219/00058* (2013.01); *B01J 2219/00065* (2013.01); *B01J 2219/00083* (2013.01); *B01J 2219/00159* (2013.01); *B01J 2219/00164* (2013.01); *B01J 2231/763* (2013.01)

(58) Field of Classification Search
CPC ................................................ C07D 307/68
USPC ........................................................ 549/485
See application file for complete search history.

(56) References Cited

FOREIGN PATENT DOCUMENTS

WO    WO 2010/111288 A2 *   9/2010

* cited by examiner

*Primary Examiner* — Taofiq A Solola
(74) *Attorney, Agent, or Firm* — William B. Miller

(57) ABSTRACT

A process is provided for carrying out an oxidation on a sprayable feed including a furanic substrate to be oxidized and a catalytically effective combination of cobalt, manganese, and bromide components for catalyzing the oxidation of the furanic substrate, which process comprises spraying the feed into a reactor vessel as a mist, supplying an oxidant, reacting the furanic substrate and the oxidant, and managing the exothermic temperature rise due to the reaction through a selection and control of the operating pressure within the reactor vessel. A crude dehydration product from the dehydration of fructose, glucose or both, including 5-hydroxymethylfurfural, can be directly oxidized by the process to produce 2,5-furandicarboxylic acid in surprisingly increased yields.

16 Claims, 1 Drawing Sheet

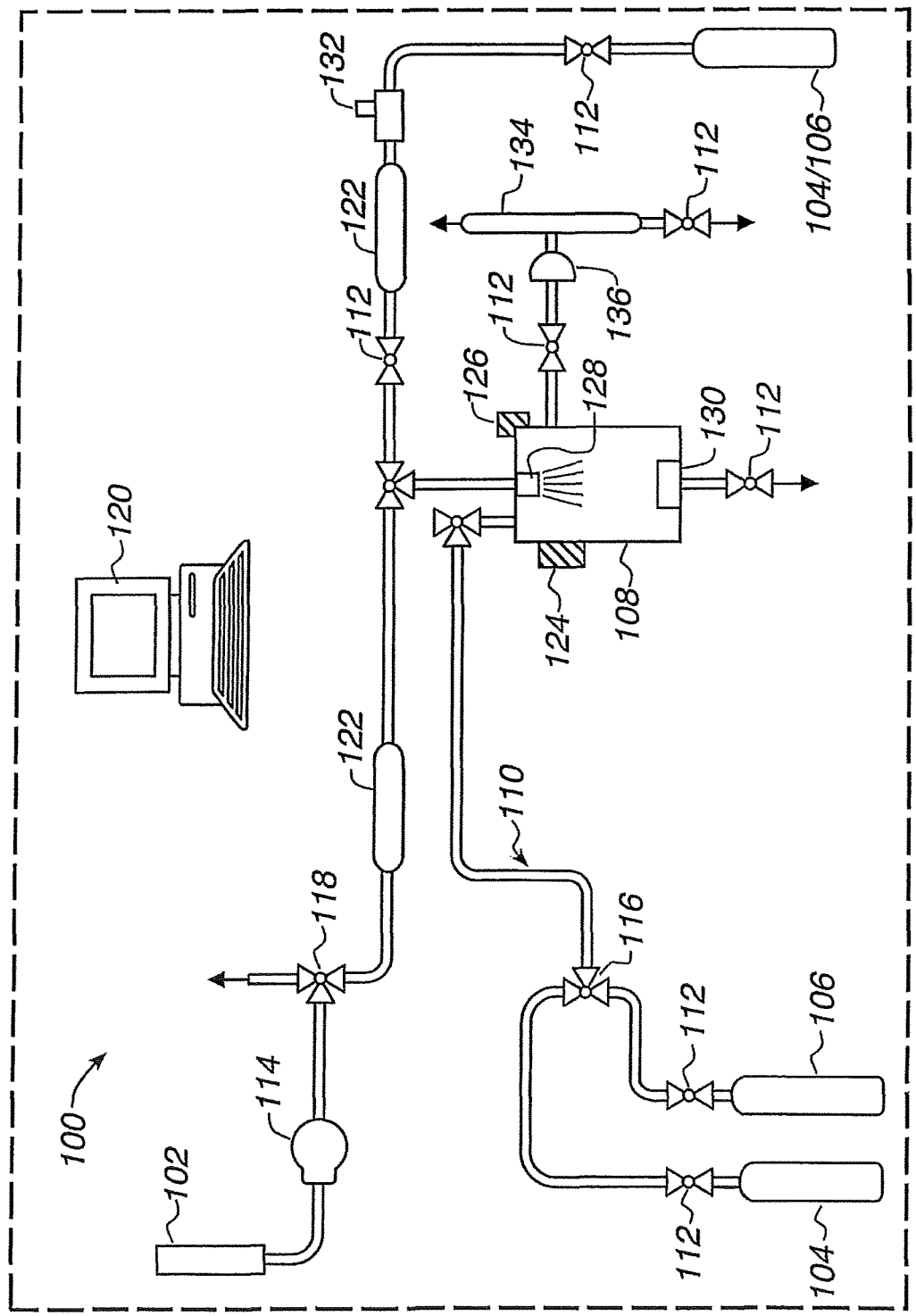

SPRAY OXIDATION PROCESS FOR PRODUCING 2,5-FURANDICARBOXYLIC ACID FROM HYDROXYMETHYLFURFURAL

BACKGROUND

The use of natural products as starting materials for the manufacture of various large-scale chemical and fuel products which are presently made from petroleum- or fossil fuel-based starting materials, or for the manufacture of biobased equivalents or analogs thereto, has been an area of increasing importance. For example, a great deal of research has been conducted into the conversion of natural products into fuels, as a cleaner and, certainly, as a more sustainable alternative to fossil-fuel based energy sources.

Agricultural raw materials such as starch, cellulose, sucrose or inulin are inexpensive and renewable starting materials for the manufacture of hexoses, such as glucose and fructose. It has long been appreciated in turn that glucose and other hexoses, in particular fructose, may be converted into other useful materials, such as 2-hydroxymethyl-5-furfuraldehyde, also known as 5-hydroxymethylfurfural or simply hydroxymethylfurfural (HMF):

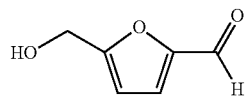

Hydroxymethylfurfural

The sheer abundance of biomass carbohydrates available provides a strong renewable resource base for the development of commodity chemical and fuel products based on HMF. For example, U.S. Pat. No. 7,385,081, issued in June 2008 to Gong, estimates, for example, that of the approximately 200 billion tons of biomass produced annually, 95% was in the form of carbohydrates, and only 3 to 4% of the total carbohydrates were then used for food and other purposes.

In view of this fact, and due to HMF's various functionalities, it has been proposed that the HMF thus obtainable from hexoses such as fructose and glucose, could be utilized to produce a wide range of products derived from renewable resources, such as polymers, solvents, surfactants, pharmaceuticals, and plant protection agents. HMF has in this regard been proposed, as either a starting material or intermediate, in the synthesis of a wide variety of compounds, such as furfuryl dialcohols, dialdehydes, esters, ethers, halides and carboxylic acids.

A number of the products discussed in the literature derive from the oxidation of HMF. Included are hydroxymethylfurancarboxylic acid (HmFCA), formylfurancarboxylic acid (FFCA), 2,5-furandicarboxylic acid (FDCA, also known as dehydromucic acid), and diformylfuran (DFF). Of these, FDCA has been discussed as a biobased, renewable substitute in the production of such multi-megaton polyester polymers as poly(ethylene terephthalate) or poly(butylene terephthalate). Derivatives such as FDCA can be made from 2,5-dihydroxymethylfuran and 2,5-bis(hydroxymethyl)tetrahydrofuran and used to make polyester polymers. FDCA esters have also recently been evaluated as replacements for phthalate plasticizers for PVC, see, e.g., WO 2011/023491A1 and WO 2011/023590A1, both assigned to Evonik Oxeno GmbH, as well as R. D. Sanderson et al., Journal of Appl. Pol. Sci. 1994, vol. 53, pp. 1785-1793.

While FDCA and its derivatives have attracted a great deal of recent commercial interest, with FDCA being identified, for instance, by the United States Department of Energy in a 2004 study as one of 12 priority chemicals for establishing the "green" chemical industry of the future, the potential of FDCA (due to its structural similarity to terephthalic acid) to be used in making polyesters has been recognized at least as early as 1946, see GB 621,971 to Drewitt et al, "Improvements in Polymer".

Unfortunately, while HMF and its oxidation-based derivatives such as FDCA have thus long been considered as promising biobased starting materials, intermediates and final products for a variety of applications, viable commercial-scale processes have proven elusive. Acid-based dehydration methods have long been known for making HMF, being used at least as of 1895 to prepare HMF from levulose (Dull, Chem. Ztg., 19, 216) and from sucrose (Kiermayer, Chem. Ztg., 19, 1003). However, these initial syntheses were not practical methods for producing HMF due to low conversion of the starting material to product. Inexpensive inorganic acids such as $H_2SO_4$, $H_3PO_4$, and HCl have been used, but these are used in solution and are difficult to recycle. In order to avoid the regeneration and disposal problems, solid sulfonic acid catalysts have also been used. The solid acid resins have not proven entirely successful as alternatives, however, because of the formation of deactivating humin polymers on the surface of the resins. Still other acid-catalyzed methods for forming HMF from hexose carbohydrates are described in Zhao et al., Science, Jun. 15, 2007, No. 316, pp. 1597-1600 and in Bicker et al., Green Chemistry, 2003, no. 5, pp. 280-284. In Zhao et al., hexoses are treated with a metal salt such as chromium (II) chloride in the presence of an ionic liquid, at 100 degrees Celsius for three hours to result in a 70% yield of HMF, whereas in Bicker et al., sugars are dehydrocyclized to HMF at nearly 70% reported selectivity by the action of sub-or supercritical acetone and a sulfuric acid catalyst.

In the acid-based dehydration methods, additional complications arise from the rehydration of HMF, which yields by-products such as levulinic and formic acids. Another unwanted side reaction includes the polymerization of HMF and/or fructose resulting in humin polymers, which are solid waste products and act as catalyst poisons where solid acid resin catalysts are employed, as just mentioned. Further complications may arise as a result of solvent selection. Water is easy to dispose of and dissolves fructose, but unfortunately, low selectivity and the formation of polymers and humin increases under aqueous conditions.

In consideration of these difficulties and in further consideration of previous efforts toward a commercially viable process for making HMF, Sanborn et al. in US Published Patent Application 2009/0156841A1 (Sanborn et al) describe a method for producing "substantially pure" HMF by heating a carbohydrate starting material (preferably fructose) in a solvent in a column, continuously flowing the heated carbohydrate and solvent through a solid phase catalyst (preferably an acidic ion exchange resin) and using differences in the elution rates of HMF and the other constituents of the product mixture to recover a "substantially pure" HMF product, where "substantially pure" is described as meaning a purity of about 70% or greater, optionally about 80% or greater, or about 90% or greater. An alternative method for producing HMF esters performs the conversion in the presence of an organic acid, which can also serve as the solvent. Acetic acid is mentioned in particular as a solvent for fructose. The resulting acetylated HMF product is reported to be "more stable" than HMF, because upon heating HMF is described as decomposing and producing byproducts "that are not easily isolated or removed," page 4, paragraph 0048.

Further, the acetylated HMF is said to be more easily recovered by distillation or by extraction, though filtration, evaporation and combinations of methods for isolating the HMF esters are also described (page 2, para. 0017). The product, HMF ester which may include some residual HMF, can then be mixed in one embodiment with organic acid, cobalt acetate, manganese acetate and sodium bromide and oxidized to FDCA in the presence of oxygen and at elevated temperatures and pressures. In the examples, a Parr reactor is used for performing the oxidation.

Those familiar with the manufacture of terephthalic acid will appreciate the fact that the same Co/Mn/Br catalyst system conventionally used in the Mid-Century Process, for liquid-phase oxidation of para-xylene to terephthalic acid, was thus shown to be useful in the oxidation of HMF esters and residual HMF to TPA's biobased analog FDCA. The capacity to source and use, for converting biobased materials, the same catalyst as used predominantly in the processing of petroleum-derived materials is a valuable and desirable feature.

Very recently published WO 2011/043661 (hereinafter, "WO'661") describes continuing efforts to produce FDCA commercially from carbohydrates such as fructose and glucose through HMF and HMF derivatives as intermediates. After summarizing their view or interpretation of previously published methods for the oxidation of HMF to FDCA in an aqueous medium using a Pt-group catalyst or involving the oxidation of HMF over a gold-based catalyst, the inventors in WO'661 contend that Sanborn et al. failed in fact to produce FDCA from the 5-(acetoxymethyl)furfural (AMF) ester formed through the reaction of HMF with the acetic acid solvent. "Surprisingly" the inventors in WO'661 find that when using an oxidation catalyst based on cobalt and manganese and containing a bromide, various furan-based materials inclusive of 5-(acetoxymethyl)furfural and other like ester derivatives of HMF can provide FDCA in "high yields" provided reaction temperatures higher than 140 degrees Celsius are employed.

The HMF ester starting materials common to both Sanborn et al. and WO'661 are indicated in WO'661 as proceeding from known methods, wherein a carbohydrate source is converted in the presence of an alkyl carboxylic acid into products comprising an HMF ester and optionally HMF. Then an HMF ester and optional HMF feed is isolated from the products for subsequent oxidation at the greater than 140 degree Fahrenheit, alleged critical temperatures. While batch, semi-continuous and continuous processes are contemplated generally, "operation in the batch mode with increasing temperature at specific times, increasing pressure at specific times, variation of the catalyst concentration at the beginning of the reaction, and variation of the catalyst composition during the reaction" is indicated as preferred (pg 4, lines 28-32). And, while the pressure in the oxidation process of WO'661 is expressly observed to be dependent on the solvent pressure, page 4, last line to page 5, line 1, the preference is that the pressure should be such that the solvent is "mainly in the liquid phase", page 5, line 2.

SUMMARY OF THE INVENTION

In contrast, the present invention, in one aspect, relates to a process for carrying out an oxidation of a sprayable feed comprising a catalytically effective combination of cobalt, manganese and bromide components with a furanic substrate to be oxidized, wherein the feed is sprayed into a reactor, combined and reacted with an oxidant therein. Further, the exothermic temperature rise within the reactor is limited at least in part by selection and control of the pressure within the reactor.

Preferably, the pressure within the reactor is selected and controlled so that the boiling point of a liquid present in the reactor as the highly exothermic oxidation proceeds (which boiling point will of course vary based on the pressure acting on the liquid) is only from 10 to 30 degrees Celsius greater than the temperature at the start of the oxidation. By selecting and controlling the pressure so that the boiling point of a liquid does not significantly exceed the temperature at the start of the oxidation, a portion of the heat generated from the oxidation process is accounted for in vaporizing the liquid and so the exothermic temperature rise within the reactor can be limited. It will be appreciated that in limiting the exothermic temperature rise, yield losses due to higher temperature byproducts and degradation products, as well as to due to solvent burning, can correspondingly be reduced.

In the HMF to FDCA process, conveniently, the same acetic acid solvent/carrier used for the HMF and the Co/Mn/Br catalyst in the WO'661 reference, in Sanborn et al., and in the Partenheimer (Adv. Synth. Catal. 2001, vol. 343, pp. 102-111) and Grushin (WO 01/72732) references described in WO'661's background can serve as the liquid, having a boiling point at modest pressures that corresponds closely to the typically desired oxidation temperatures. The vaporization of acetic acid in this case offers a further benefit, as well. While the various components of the feed and while intermediates in the conversion of HMF to its oxidized derivative FDCA remain soluble in the acetic acid, FDCA is minimally soluble in acetic acid and thus can precipitate out (either in the reactor itself and/or upon cooling the reaction mixture exiting the reactor) and be recovered as a substantially pure solid product.

In a second aspect, the present invention provides a fundamental improvement in the oxidation of a biobased furanic substrate to produce FDCA as variously addressed in the past by Sanborn et al., by WO'661, by the Partenheimer and Grushin references, as well as WO 2010/132740 to Sanborn. As discussed above, the tendency of HMF to self-polymerize and degrade in acidic environments and at elevated temperatures has led to efforts in recent years to derivatize HMF to a more stable intermediate that can still be oxidized to produce FDCA. In this second aspect, a process is provided for making FDCA from fructose, glucose or a combination thereof, based upon the discovery that in the context of the inventive spray oxidation process using a Co/Mn/Br Mid-Century Process-type oxidation catalyst, the crude dehydration product mixture resulting from a conventional acid dehydration of the carbohydrate can be directly solubilized in the solvent, sprayed into the reactor and oxidized with subsequent recovery of the FDCA product in an unexpectedly high yield. No isolation or purification of the HMF is required, and no derivatization of the HMF is needed (though the present invention extends to such HMF derivatives as furanic substrates that can be oxidized). In fact, as established in the Examples below, use of a crude dehydration product (crude HMF) can provide greater than 100 percent yield of FDCA based on the HMF content of the feed coming into the oxidation process.

DESCRIPTION OF THE FIGURE

FIG. 1 is a schematic diagram of an illustrative embodiment of an oxidation reaction system.

DETAILED DESCRIPTION OF CERTAIN EMBODIMENTS

The present invention may be more completely understood by describing certain embodiments in greater detail. These embodiments are not to be taken as limiting the scope and breadth of the current invention as more particularly defined in the claims that follow, but are illustrative of the principles behind the invention and demonstrate various ways and options for how those principles can be applied in carrying out the invention.

One embodiment of a process for carrying out an oxidation of a sprayable feed which comprises a catalytically effective combination of cobalt, manganese and bromide components with a furanic substrate to be oxidized, involves spraying the feed into a reactor and combining and reacting the furanic substrate in the feed with an oxidant (such as an oxidizing gas), while managing and limiting the exothermic temperature rise within the reactor by selection and control of the pressure within the reactor.

While a variety of furanic substrates can be contemplated for oxidation according to the inventive process, preferably the furanic substrates are those derived in whole or in significant part from renewable sources and that can be considered as "biobased" or "bioderived", These terms may be used herein identically to refer to materials whose carbon content is shown by ASTM D6866, in whole or in significant part (for example, at least about 20 percent or more), to be derived from or based upon biological products or renewable agricultural materials (including but not limited to plant, animal and marine materials) or forestry materials. In this respect ASTM Method D6866, similar to radiocarbon dating, compares how much of a decaying carbon isotope remains in a sample to how much would be in the same sample if it were made of entirely recently grown materials. The percentage is called the biobased content of the product. Samples are combusted in a quartz sample tube and the gaseous combustion products are transferred to a borosilicate break seal tube. In one method, liquid scintillation is used to count the relative amounts of carbon isotopes in the carbon dioxide in the gaseous combustion products. In a second method, 13C/12C and 14C/12C isotope ratios are counted (14C) and measured (13C/12C) using accelerator mass spectrometry. Zero percent 14C indicates the entire lack of 14C atoms in a material, thus indicating a fossil (for example, petroleum based) carbon source. One hundred percent 14C, after correction for the post-1950 bomb injection of 14C into the atmosphere, indicates a modern carbon source. ASTM D6866 effectively distinguishes between biobased materials and petroleum derived materials in part because isotopic fractionation due to physiological processes, such as, for example, carbon dioxide transport within plants during photosynthesis, leads to specific isotopic ratios in natural or biobased compounds. By contrast, the 13C/12C carbon isotopic ratio of petroleum and petroleum derived products is different from the isotopic ratios in natural or bioderived compounds due to different chemical processes and isotopic fractionation during the generation of petroleum. In addition, radioactive decay of the unstable 14C carbon radioisotope leads to different isotope ratios in biobased products compared to petroleum products.

More particularly, preferred furanic substrates are those which can be derived from readily available carbohydrates from agricultural raw materials such as starch, cellulose, sucrose or inulin, especially fructose, glucose or a combination of fructose and glucose, though any such carbohydrate source can be used generally. Examples of suitable carbohydrate sources that can be used to provide the furanic substrates of interest include, but are not limited to, hexose, fructose syrup, crystalline fructose, and process streams from the crystallization of fructose. Suitable mixed carbohydrate sources may comprise any industrially convenient carbohydrate source, such as corn syrup. Other mixed carbohydrate sources include, but are not limited to, hexoses, fructose syrup, crystalline fructose, high fructose corn syrup, crude fructose, purified fructose, high fructose corn syrup refinery intermediates and by-products, process streams from crystallizing fructose or glucose or xylose, and molasses, such as soy molasses resulting from production of soy protein concentrate, or a mixture thereof.

Especially of interest are the furanic substrates of this natural carbohydrate-derived character, which can be spray oxidized in the presence of a homogeneous oxidation catalyst contained in a sprayable feed including the furanic substrate, to provide products of commercial interest such as 2,5-furandicarboxylic acid (FDCA). In WO'661, for example, a variety of furanic substrates are identified which can be oxidized in the presence of mixed metal bromide catalysts, such as Co/Mn/Br catalysts, to provide FDCA—5-hydroxymethylfurfural (HMF), esters of HMF, 5-methylfurfural, 5-(chloromethyl)furfural, 5-methylfuroic acid, 5-(chloromethyl)furoic acid and 2,5-dimethylfuran (as well as mixtures of any of these) being named.

Most preferably, however, the furanic substrates which are fed to the process are simply those which are formed by an acid-catalyzed dehydration reaction from fructose, glucose or a combination of these according to the various well-known methods of this character, principally comprising HMF and the esters of HMF formed with an organic acid or organic acid salt.

As has been indicated previously, one such organic acid, acetic acid, has been found especially useful as a solvent for the subsequent Co/Mn/Br-catalyzed oxidation of HMF and HMF esters, such as the 5-(acetoxymethyl)furfural (AcHMF) ester of HMF and acetic acid. Acetic acid as noted in the WO'661 reference is helpfully regenerated from AcHMF through the oxidation step, and is a good solvent for the HMF and its derivatives but is not a good solvent for FDCA—substantially simplifying separation and recovery of a substantially pure FDCA solid product. Further, as noted by Sanborn et al., AcHMF and HMF can be oxidized together to yield the single FDCA product in reasonable yields. In the context of the present invention, acetic acid has the still added beneficial attribute of having a boiling point at reasonable pressures that is within the desired range of 10 degrees to 30 degrees Celsius above the preferred temperature range for carrying out the Co/Mn/Br-catalyzed oxidation of the HMF and HMF esters to FDCA, so that by selecting an operating pressure and also controlling the system pressure to maintain the acetic acid solvent's boiling point in this range, an evaporative heat sink can be provided in the reaction system to limit the exothermic heat rise that ensues as the HMF and HMF esters are oxidized. Temperature-related yield losses of substrate to byproducts and solvent loss to burning can accordingly be limited by this means and by further optimization of catalyst composition, water concentration and substrate addition modes (as demonstrated below).

Given the usefulness of acetic acid for the subsequent oxidation step, the acid dehydration of carbohydrates would in one embodiment be accomplished simply through the use of acetic acid in a concentrated, preferably highly concentrated form, an elevated temperature consistent with a preheating to the oxidation temperatures used thereafter and a sufficient residence time in a first, dehydration reactor to substantially fully convert all of the carbohydrates before the crude dehydration product mix would be combined with the Co/Mn/Br catalyst components and made into a sprayable feed composition. Alternatively, a solid phase acid catalyst could also be used in the first dehydration reactor to assist in converting the carbohydrates in a feed wherein the crude dehydration product mix from a first reactor is made into a sprayable feed for a subsequent spray oxidation reactor. It will be appreciated that other organic acids and even the strong inorganic acids that have been traditionally used for making HMF from fructose, for example, could equally be used for the dehydration, so that any acid or combination of acids is generally contemplated, provided that the oxidation step to come thereafter is not materially adversely affected by the selection—for example, by deactivation of the Co/Mn/Br catalyst or other effects. It is expected however that a useful approach would be to use a concentrated acetic acid solution and a solid acid catalyst in the first reactor for performing the dehydration step.

For example, a continuous process can be envisioned wherein a fructose/acetic acid mixture is supplied to a reactor vessel containing a solid acid catalyst at 150 degrees Celsius. The fructose is dehydrated to HMF and the HMF substantially completely converted to AcHMF ester with excess acetic acid, and then the crude dehydration mixture is made into a sprayable feed with the Co/Mn/Br catalyst in a subsequent vessel. The resulting sprayable feed is then continuously supplied to the second, oxidation step. The acetic acid would preferably be sufficiently concentrated so that, given the amount of water produced in the dehydration step, the crude dehydration product mix contains not more than 10 weight percent of water and preferably contains not more than 7 weight percent of water.

The solid phase acid catalysts useful for the dehydration step in such a scenario include acidic resins such as Amberlyst 35, Amberlyst 15, Amberlyst 36, Amberlyst 70, Amberlyst 131 (Rohm and Haas); Lewatit 52328, Lewatit K2431, Lewatit 52568, Lewatit K2629 (Bayer Company); and Dianion SK104, PK228, RCP160, Relite RAD/F (Mitsubishi Chemical America, Inc.). Other solid phase catalysts such as clays and zeolites such as CBV 3024 and CBV 5534G (Zeolyst International), T-2665, T-4480 (United Catalysis, Inc), LZY 64 (Union Carbide), H-ZSM-5 (PQ Corporation) may also be useful, along with sulfonated zirconia or a Nafion sulfonated tetrafluoroethylene resin. Acidic resins such as Amberlyst 35 are cationic, while catalysts such as zeolite, alumina, and clay are porous particles that trap small molecules. Because the dehydration step will produce water, a cation exchange resin having a reduced water content is preferred for carrying out the dehydration step. A number of commercially available solid phase catalysts, such as dry Amberlyst 35, have approximately 3% water content and are considered preferable for this reason.

The crude dehydration product mix thus generated is then input as part of a sprayable feed to a spray oxidation process of a type described in WO 2010/111288 to Subramaniam et al. (WO'288), which published application is hereby incorporated by reference herein. In one embodiment, the sprayable feed—in addition to containing the AcHMF esters and potentially some residual HMF, but containing substantially no unreacted carbohydrates, comprises acetic acid and preferably no more than 10 weight percent of water as described above, as well as a homogeneous oxidation catalyst dissolved in the sprayable feed. In other embodiments, more generally, the sprayable feed comprises one or more furanic substrate species to be oxidized, a homogeneous oxidation catalyst, a solvent for the furanic substrate species and the homogeneous oxidation catalyst, a limited amount of water and optionally other materials for improving the spraying or processing characteristics of the sprayable feed, for providing additional evaporative cooling or other purposes.

The sprayable feed can include at least one liquid whose boiling point under normal operating pressures is from 10 to 30 degrees Celsius greater than the temperature at which the oxidation reaction is begun. The liquid in question may be, or include, the solvent, or optionally other liquids can be selected to provide the evaporative cooling for limiting the exothermic temperature rise in the reactor as the reaction proceeds. Preferably acetic acid functions both as a solvent and as a vaporizable liquid for providing evaporative cooling as the reaction proceeds.

As described in the WO'288 reference, the spray process is configured to produce a high number of small droplets into which oxygen (from an oxygen-containing gas used as the oxidant) is able to permeate and react with the AcI-IMF esters therein, the droplets functioning essentially as microreactors and with the substrate oxidation to FDCA substantially occurring within the droplets.

The spray oxidation process is operated in a manner to avoid combustion of the solvent to the extent possible, as well as to avoid the temperature-related formation of yield-reducing byproducts, in part by selection of and management of the "normal operating pressures" just referenced so as to limit the exothermic temperature rise in the reactor through evaporative cooling. Preferably, consistent evaporative cooling control is enabled in respect of the exothermic temperature rise by maintaining a vapor/liquid equilibrium for the solvent in the reactor. In practice, this can be done by maintaining a substantially constant liquid level in the reactor, so that the rate of evaporation of acetic acid and water is matched by the rate at which condensed acetic acid and water vapor are returned to the reactor. Additional heat removal devices, such as internal cooling coils and the like, can also be used. Preferably, the sprayable feed is sprayed into a reactor containing $O_2$ in an inert background gas in the form of fine droplets (e.g., as a mist). The droplets can be formed as small as possible from a spray nozzle, such as a nebulizer, mister, or the like. Smaller droplets containing the furanic substrate(s) to be oxidized result in an increased interfacial surface area of contact between the liquid droplets and gaseous $O_2$. The increased interfacial surface area can lead to improved reaction rates and product quality (e.g., yield and purity). Also, the droplets are sufficiently small such that the $O_2$ penetrates the entire volume of the droplets by diffusion and is available at stoichiometric amounts throughout the droplet for the selective oxidation to proceed to the desired product. As well, smaller droplets are more readily vaporized to provide efficient evaporative cooling of the highly exothermic oxidation reaction. Preferably, the sprayable feed is supplied to the reactor in the form of droplets having a mean droplet size of from 300 microns to 1000 microns, more preferably from 100 microns to 300 microns, and still more preferably from 10 to 100 microns.

FIG. 1 shows a diagram of an embodiment of the illustrative oxidation system 100 which can include a source 102 of the sprayable feed, an oxygen or oxygen containing-gas (for example, air and oxygen-enriched air) source 104, and a diluent gas (e.g., noble gases, nitrogen, carbon dioxide) source 106, in fluid communication with a reactor 108, such as through fluid pathways 110. Fluid pathways 110 are shown by the tubes that connect the various components together, such as, for example, sprayable feed source 102 which is fluidly coupled to a pump 114, splitter 118 and heater 122, all before the sprayable feed is passed through the nozzles 128. The fluid pathways 110 can include one or more valves 112, pumps 114, junctions 116, and splitters 118 to allow fluid flow through the fluid pathways 110. Accordingly, the arrangement can be configured to provide for selectively transferring a sprayable feed, oxygen or oxygen-containing gases (oxygen by itself being preferred), and one or more diluent gases to the reactor 108 so that an oxidation reaction can be performed as described.

Additionally, the oxidation system 100 can include a computing system 120 that can be operably coupled with any of the components of the oxidation system 100. Accordingly, each component, such as the valves 112 and/or pumps 114 can receive instructions from the computing system 120 with regard to fluid flow through the fluid pathways 110. General communication between the computing system 120 and oxidation system components 100 is represented by the dashed-line box around the oxidation system 100. The computing system 120 can be any type of computing system ranging from personal-type computers to industrial scale computing systems. Also, the computing system can include a storage medium, such as a disk drive, that can store computer-executable instructions (e.g., software) for performing the oxidation reactions and controlling the oxidation system 100 components.

The fluid pathway 110 that fluidly couples the sprayable feed source 102 may include a heater 122 as shown. The heater 122 can pre-heat the sprayable feed to a desired temperature before the feed is introduced into the reactor 108. As shown, the fluid pathway 110 that fluidly couples any of the gas sources 104, 106 to the reactor 108 can similarly include a heater 122 to heat the gases to a temperature before these are introduced into the reactor 108. Any of the heaters 122 can be operably coupled with the computing system 120 so that the computing system 120 can provide operation instructions to the heater 122, and/or the heater 122 can provide operation data back to the computing system 120. Thus, the heaters 122, as well as any of the components, can be outfitted with data transmitters/receivers (not shown) as well as control modules (not shown).

The fluid pathways 110 can be fluidly coupled with one or more nozzles 128 that are configured to spray the sprayable feed (and optionally including the oxygen-containing and/or diluent gases from 104 and 106, if nozzles 128 are employed for injecting both gases and liquids or a mixture of gases and liquids) into the reactor 108. The nozzles 128 in any such arrangements can be configured to provide liquid droplets of the sprayable feed at an appropriately small size as described above, distributed across a cross-section of the reactor 108. While FIG. 1 shows the nozzles 128 pointed downward, the nozzles 128 in fact can be in any orientation and as a plurality of nozzles 128 can be configured into any arrangement. Similarly, the droplets may be formed by other methods, such as by ultrasound to break up a jet of the sprayable feed. Generally speaking, given the role of the droplets as micro-reactors for carrying out the oxidation process, it will be appreciated that a narrower droplet size distribution from the nozzles 128 and across a cross-section of the reactor 108 will be preferable for providing consistent reaction conditions (from micro-reactor to micro-reactor), and the type, number and spatial orientation and configuration of the nozzles 128 will be determined at least in part with this consideration in mind.

The reactor 108 in one embodiment can include a tray 130 that is configured to receive oxidation product. As oxidation product is formed, it can fall out of the droplets, such as by precipitation, and land on the tray 130. Also, the tray 130 can be a mesh, filter, and membrane or have holes that allow liquid to pass through and retain oxidation product. Any type of tray 130 that can catch oxidation product can be included in the reactor 108. Alternatively, the oxidation product can be removed with the liquid from the reactor 108, and subsequently separated therefrom.

The reactor 108 can be outfitted with a temperature controller 124 that is operably coupled with the computing system 120 and can receive temperature instructions therefrom in order to change the temperature of the reactor 108. As such, the temperature controller 124 can include heating and/or cooling components as well as heat exchange components. The temperature controller 124 can also include thermocouples to measure the temperature and can provide the operating temperature of the reactor 108 to the computing system 120 for analysis.

The reactor 108 can be outfitted with a pressure controller 126 that is operably coupled with the computing system 120 and can receive pressure instructions therefrom in order to change the operating pressure in the reactor 108. As such, the pressure controller 126 can include compressors, pumps, or other pressure modulating components. The pressure controller 126 can also include pressure measuring devices (not shown) to measure the pressure of the reactor and can provide the operating pressure of the reactor 108 to the computing system 120 for analysis. Pressure control is preferably further provided by back pressure regulator 136 in the line 110 leading to gas/liquid separator 134, which functions as described herein to help maintain a vapor/liquid equilibrium in the reactor 108 (for providing evaporative cooling as a restraint on the oxidative temperature rise in the reactor 108) through withdrawing liquid from the reactor 108 through a heated metering valve 112 at approximately the same rate of its addition to the reactor 108. In addition, a liquid level controller system (such as an optic fiber coupled to the micro-metering valve 112) may be employed to maintain the liquid phase level (and therefore the liquid phase holdup) constant in the reactor.

Additionally, the oxidation system 100 can include a mass flow controller 132 that is fluidly coupled to the sprayable feed source 102 and optionally to one or more of the gas sources where the sprayable feed is charged with gas (e.g., oxygen, oxygen-containing gas, inert gas and/or diluent gas) before being sprayed from the nozzles 128. The mass flow controller 132 can be configured such that the computing system 120 can modulate the amount of gas (or gases) charged into the sprayable feed, which in turn can modulate the size of the droplets that are sprayed from the nozzles 128. Thus, the mass flow controller 132 can be used to feed an energizing gas into the sprayable feed and then through the nozzles 128 to assist in forming small droplets.

The oxidation system 100 of FIG. 1 can include components that are made of standard materials that are commonly used in storage containers, storage tanks, fluid pathways, valves, pumps, and electronics. Also, the reactor and the nozzles can be prepared from oxidation resistive materials. For example, the reactor can include a titanium pressure vessel equipped with a heater, a standard solution pump, and ceramic spray nozzles. A high pressure liquid chromatography (HPLC) solution reciprocating pump or a non-reciprocating piston pump are available to feed the sprayable feed through the nozzles 128. The sprayable feed (and the various gases) can be pre-heated to the reaction temperature by a tubular heater associated with the reactor.

Also, the reactor can include liquid solvent in a predetermined amount before receiving the sprayable feed and/or gases. The liquid solvent can be the same solvent that is included in the sprayable feed, heated before introduction of the sprayable feed to a temperature at or about the boiling point of the solvent at the system's operating pressure. The temperature/pressure can allow for the solvent to boil so that there is solvent vapor within the reactor before conducting the oxidation reaction. The amount of solvent that is boiled or vaporized can be allowed to reach an equilibrium or saturated state so that the liquid solvent with the sprayable feed is inhibited from vaporizing as the feed is sprayed into the reactor, except in response to the exothermicity of the oxidation reaction, and so that the catalyst and furanic substrates in the sprayable feed are not caused to precipitate within the droplets as the solvent evaporates. In addition, the $O_2$-containing stream that is admitted into the reactor may be sparged through the liquid phase at the bottom of the spray reactor such that the stream not only saturates that liquid phase with oxygen but the stream itself is saturated with acetic acid. The acetic acid-saturated gas stream rises up the tower and helps replenish the acetic acid vapor that is continuously removed from the reactor by the effluent gas stream. It is important that an adequate equilibrium between the acetic acid in the spray phase and that in the vapor phase is maintained to prevent substantial evaporation of the entering acetic acid into the vapor phase that might cause the catalyst to precipitate out.

The homogeneous oxidation catalyst included in the sprayable feed can be selected from a variety of oxidation catalysts, but is preferably a catalyst based on both cobalt and manganese and suitably containing a source of bromine, preferably a bromide. The bromine source in this regard can be any compound that produces bromide ions in the sprayable feed, including hydrogen bromide, sodium bromide, elemental bromine, benzyl bromide and tetrabromoethane. Bromine salts, such as an alkali or alkaline earth metal bromide or other metal bromide such as zinc bromide can be used. Preferably the bromide is included via hydrogen bromide or sodium bromide. Still other metals have previously been found useful for combining with Co/Mn/Br, for example, Zr and/or Ce (see Partenheimer, Catalysis Today, vol. 23, no. 2, pp 69-158 (1995)), and may be included as well.

Each of the metal components can be provided in any of their known ionic forms. Preferably the metal or metals are in a form that is soluble in the reaction solvent. Examples of suitable counterions for cobalt and manganese include, but are not limited to, carbonate, acetate, acetate tetrahydrate and halide, with bromide being the preferred halide. With acetic acid as the solvent for the sprayable feed, the acetate forms of Co and Mn are conveniently used.

For a Co/Mn/Br catalyst in the context of making FDCA from a crude fructose acid dehydration product, for example, in the spray oxidation process of the present invention, typical molar ratios of Co:Mn:Br are about 1:1:6, though preferably the metals will be present in a molar ratio of 1:1:4 and most preferably a 1:1:2 ratio will be observed. The total catalyst concentration will typically be on the order of from 0.4 to 2.0 weight percent of the sprayable feed, though preferably will be from 0.6 to 1.6 percent by weight and especially from 0.8 to 1.2 percent by weight of the sprayable feed.

The solvent for the system and process can be any organic solvent that can dissolve both the furanic substrate(s) to be oxidized and the oxidation catalyst as just described, though with respect to limiting the exothermic temperature rise caused by the oxidation, the solvent will preferably also have a boiling point that is from about 10 to about 30 degrees higher than the desired reaction temperatures, at the operating pressures where one would conventionally wish to practice. Preferred solvents will, moreover, be those in which the desired oxidized product or products will have limited solubility, so that the desired products readily precipitate within the droplets of sprayable feed as the products are formed and are readily recovered in a substantially pure solid form. Particularly suitable solvents for the Co/Mn/Br catalyst and furanic substrates are those containing a monocarboxylic acid functional group. Of these, the aliphatic C2 to C6 monocarboxylic acids can be considered, though the boiling points of the C3+ acids are such that acetic acid is strongly favored. Aqueous solutions of acetic acid may be used, though as has been mentioned, the water content should preferably be limited in the context of a process (typically continuous) wherein the crude dehydration products from the first, dehydration reactor are used directly to make up the sprayable feed, so that the total water content of the sprayable feed including water from the dehydration step is 10 weight percent or less, and especially 7 weight percent or less.

The feed rate of the furanic substrate(s) to the oxidation reactor will preferably be controlled to allow satisfactory control over the exothermic temperature rise to be maintained through evaporative cooling and optional external cooling/thermal management means. Accordingly, the furanic substrate portion of a liquid sprayable feed will typically comprise 1 to 10 percent by weight of the sprayable feed, with corresponding amounts of sugars in the feed to a first, dehydration step where the crude dehydration product is to be used directly to make up the sprayable feed to the second, oxidation step. The feed rate of the gas stream contain the oxidant ($O_2$) is such that the molar input rate of $O_2$ corresponds to at least the stoichiometric amount needed to form FDCA based on the molar substrate addition rate. Typically, the feed gas contains at least 50% by volume of an inert gas, preferably $CO_2$, in order to ensure that there are no flammable vapors.

In one embodiment, the sprayable feed in the form of a fine mist spray is contacted with the oxygen in the gaseous reaction zone with the reaction temperature being in a range of 160 to 220° C., more preferably 170 to 210° C., or 180 to 200° C. when the solvent is acetic acid, and the operating pressure is selected and controlled (by means of continuously removing gases and liquids from the reaction space as gas and liquids are input, and by means of a back-pressure regulator in the gas line from the reaction space and a suitable regulating valve in the liquid and solids effluent line from the reaction space) at from 10 bars to 60 bars, preferably 12 to 40 bars, or 15 to 30 bars. The sprayable feed and/or any gases input to the reactor either with the sprayable feed or independently thereof are preferably preheated to substantially reaction temperatures prior to being introduced into the gaseous reaction zone.

The rapid oxidation of the furanic substrate(s) characterizing the present spray oxidation process (at the preferred pressure and reactor temperature ranges) assists in preventing the kind of degradation and related yield losses seen with previous efforts to produce FDCA from HMF, for example, and also helps prevent yield losses to solvent burning as the acetic acid or other solvent is vaporized, passes from the reactor, is condensed and recycled as part of additional sprayable feed. In this regard, the nozzles 128 can be designed and arrayed to produce droplets of a size so that in passing from the nozzles 128 to the reservoir of bulk liquid maintained in the reactor for keeping a vapor-liquid equilibrium (and taking into account coalescence of droplets within the reactor as well as progressive vaporization of the droplets in the reactor), the substrate(s) are substantially oxidized as the droplets emerge from the nozzles 128 and so that substantially no oxidation of the furanic substrate(s) takes place in the bulk liquid. At the same time, since the oxidation of the solvent is not as fast as the oxidation of the furanic substrate(s), the contact time between the oxygen and the solvent can be limited in the droplet phase to that necessary for achieving the desired degree of oxidation of the furanic substrate(s) in the droplets, and kept to acceptable levels in the bulk liquid as it is continually withdrawn from the reactor.

The "average residence time" of the sprayable feed during continuous reactor operation thus can be understood in terms of the ratio of the steady volumetric holdup of the bulk liquid to the volumetric flow rate of the sprayable feed. In one embodiment, the average residence time for the sprayable fed in the reactor is from 0.01 minutes, preferably from 0.1 minutes and especially from 0.5 minutes to 1.4 minutes.

The present invention is more particularly illustrated by the examples which follow:

EXAMPLES

For the examples that follow, unless otherwise noted, certain apparatus and procedures were used:

Reactor unit: The test reactor unit is a mechanically-stirred high-pressure Parr reactor (50-mL titanium vessel with view windows rated at 2800 psi and 300° C.) that is equipped with a Parr 4843 controller for the setup and control of reaction temperature and stirring speed. Reactor pressure measurements were accomplished via a pressure transducer attached to the reactor. Temperature, pressure and stirring speed are recorded by a LabView@ data acquisition system.

Materials Used and General Procedure: Pure 5-hydroxymethylfurfural (HMF, 99% purity) was supplied by Aldrich. Crude HMF 4956-57 (21% purity) and 5345-82 (60% purity) lots were supplied by Archer Daniels Midland Company and contained significant amounts of the HMF dimer (5,5'-[oxy-bis(methylene)]bis-2-furfural, or OBMF) and other humins, the polymers formed via the self-polymerization of HMF. All the catalysts, additives, substrates and solvents were used as received without further purification. Industrial grade (≥99.9% purity, <32 ppm $H_2O$, <20 ppm THC) liquid $CO_2$ and ultra high purity grade oxygen were purchased from Linweld.

The semi-continuous oxidation of HMF to 2,5-furandicarboxylic acid (FDCA) was carried out in the 50 mL titanium Parr reactor. Typically, a pre-determined amount of $N_2$ or $CO_2$ was first added to the reactor containing roughly 30 mL acetic acid solution in which known concentrations of substances containing the catalytic components (Co, Mn and Br) were dissolved. The reactor contents were then heated to the reaction temperature following which $O_2$ was added until the selected final pressure was reached. The partial pressures of $O_2$ and the diluent were known. A solution of HMF in acetic acid was subsequently pumped into the reactor at a pre-defined rate to initiate the reaction. The total reactor pressure was maintained constant by continuously supplying fresh $O_2$ from a 75-mL stainless-steel reservoir to compensate for the oxygen consumed in the reaction. The pressure decrease observed in the external oxygen reservoir was used to monitor the progress of the reaction.

Following the reaction (i.e., after a known amount of the HMF solution was pumped into the reactor and the $O_2$ consumption leveled off), the reaction mixture was cooled to room temperature.

The gas phase was then sampled and analyzed by gas chromatography (GC) (Shin Carbon ST 100/120 mesh) to determine the yields of CO and $CO_2$ produced by solvent and substrate burning.

The insoluble FDCA product was separated from the liquid mixture by filtration and the solid was washed with acetic acid to remove most of the soluble impurities. The resulting white solid was dried in an oven at 100° C. for 2 hrs to remove absorbed solvent. HPLC and $^1H$ NMR analyses revealed substantially pure FDCA. The reactor was washed with acetic acid and methanol to recover any residual FDCA solid. This extract along with the filtrate that was retained after isolation of the solid FDCA were analyzed by HPLC (C18 ODS-2 column) to determine the composition of the liquids. The overall yields of the oxidation products reported below were based on the compositions of the solid and liquid phases. All percentages are expressed as mole percent unless otherwise specified.

Examples 1-11

For Examples 1-11, different amounts of $Co(OAc)_2 \cdot 4H_2O$, $Mn(OAc)_2 \cdot 4H_2O$ and HBr in a mixture of 30 mL HOAc and 2 mL $H_2O$ were placed in the 50 mL titanium reactor and pressurized with 5 bar inert gas ($N_2$ or $CO_2$). The reactor was heated to the reaction temperature, followed by the addition of inert gas until the reactor pressure was 30 bar. After the introduction of 30 bar $O_2$ (for a total reactor pressure of 60 bars), 5.0 mL of an HOAc solution containing dissolved pure/refined HMF (13.2 mmol) was continuously pumped into the reactor at a constant rate of 0.25 mL/min (total pumping time was therefore 20 minutes). The reaction mixture was vigorously stirred at the reaction temperature throughout the pumping duration and for another 10 minutes following addition of the HMF/HOAc solution. Then the reactor was rapidly cooled to room temperature for product separation and analysis. The results are summarized in Table 1.

TABLE 1

Effect of catalyst composition on the oxidation of HMF [a]

| Ex. | $Co^{2+}$ mmol | $Mn^{2+}$ mmol | $Br^-$ mmol | Inert gas | T (° C.) | $Y_{FDCA}$[b] (%) | $Y_{FFCA}$[b] (%) | $Y_{DFF}$[b] (%) | CO/HMF (mol/mol) | $CO_2$/HMF[d] (mol/mol) |
|---|---|---|---|---|---|---|---|---|---|---|
| 1 | 1.1 | 0.033 | 1.1 | $N_2$ | 160 | 66.0 | 0.4 | 1.6 | 0.106 | 0.363 |
| 2 | 2.2 | 0.033 | 1.1 | $N_2$ | 160 | 78.1 | 0 | 0.1 | 0.111 | 0.440 |
| 3 | 1.1 | 0.033 | 1.1 | $N_2$ | 180 | 73.0 | 0 | 0.2 | 0.174 | 0.455 |

TABLE 1-continued

Effect of catalyst composition on the oxidation of HMF [a]

| Ex. | $Co^{2+}$ mmol | $Mn^{2+}$ mmol | $Br^-$ mmol | Inert gas | T (° C.) | $Y_{FDCA}$[b] (%) | $Y_{FFCA}$[b] (%) | $Y_{DFF}$[b] (%) | CO/HMF (mol/mol) | $CO_2$/HMF[d] (mol/mol) |
|---|---|---|---|---|---|---|---|---|---|---|
| 4 | 2.2 | 0.033 | 1.1 | $N_2$ | 180 | 78.5 | 0 | 0.1 | 0.189 | 0.519 |
| 5 | 1.1 | 0.033 | 1.1 | $CO_2$ | 180 | 77.9 | 0 | 0.1 | 0.200 | — |
| 6 | 2.2 | 0.033 | 1.1 | $CO_2$ | 180 | 83.3 | 0 | 0.1 | 0.267 | — |
| 7[c] | 2.2 | 0 | 1.1 | $CO_2$ | 170 | 62.4 | 0.1 | 0.7 | 0.214 | — |
| 8 | 2.2 | 0.033 | 1.1 | $CO_2$ | 170 | 81.4 | 0 | 0.1 | 0.176 | — |
| 9 | 2.2 | 0.066 | 1.1 | $CO_2$ | 170 | 82.4 | 0 | 0 | 0.156 | — |
| 10 | 2.2 | 0.13 | 1.1 | $CO_2$ | 170 | 82.0 | 0 | 0 | 0.126 | — |
| 11 | 2.2 | 0.26 | 1.1 | $CO_2$ | 170 | 79.0 | 0 | 0 | 0.113 | — |

[a] Conversion of HMF >99% for all the reactions;
[b] $Y_{FDCA}$: Overall yield of 2,5-furandicarboxylic acid,
$Y_{FFCA}$: Overall yield of 5-formylfurancarboxylic acid,
$Y_{DFF}$: Overall yield of 2,5-diformylfuran;
[c] The reaction was run for 40 minutes following HMF addition because of long induction period;
[d] Reliable analysis not possible when $CO_2$ is used as the inert gas.

As shown in Table 1, the yields of FDCA increased with an increase of cobalt amount from 1.1 to 2.2 mmol, especially when the reaction temperature was 160 deg. C. The presence of a small amount of manganese (a) reduced the induction period for the main reaction (as inferred from the $O_2$ consumption profiles), (b) increased the FDCA yield (compare Examples 7 and 8) and (c) reduced the yield of gaseous by-product CO. While further increase of manganese amount to above 0.13 mmol had no beneficial effect on the yield of FDCA, the yield of CO kept decreasing.

Examples 12-18

2.2 mmol $Co(OAc)_2 \cdot 4H_2O$, 0.033 mmol $Mn(OAc)_2 \cdot 4H_2O$ and 1.1 mmol HBr were dissolved in various mixtures of HOAc and $H_2O$ with different volumetric ratios (total volume 32 mL). Each mixture was placed in the 50-mL titanium reactor and pressurized with 5 bar $N_2$. The reactor was heated to 180° C. followed by the addition of $N_2$ until the reactor pressure was 30 bar and then 30 bar $O_2$ until the total reactor pressure was 60 bar. Following this, 5.0 mL of an HOAc solution containing dissolved pure (99%) HMF (13.2 mmol) was continuously pumped into the reactor at a constant rate of 0.25 mL/min (total pumping time was therefore 20 minutes). The reaction mixture was vigorously stirred at 180° C. throughout the pumping duration and for another 10 minutes following addition of the HMF/HOAc solution. Then the reactor was rapidly cooled to room temperature for product separation and analysis. The results are summarized in Table 2.

TABLE 2

Effect of water concentration on the oxidation of HMF [a]

| Example# | Water conc. (v %) | $Y_{FDCA}$[b] (%) | $Y_{FFCA}$[b] (%) | CO/HMF (mol/mol) | $CO_2$/HMF (mol/mol) |
|---|---|---|---|---|---|
| 12 | 0 | 79.5 | 0 | 0.469 | 0.780 |
| 13 | 3.5 | 77.3 | 0 | 0.281 | 0.675 |
| 14 | 7.0 | 78.5 | 0 | 0.189 | 0.519 |
| 15 | 10.7 | 82.6 | 0 | 0.172 | 0.578 |
| 16 | 16.9 | 76.3 | 0 | 0.145 | 0.596 |
| 17 | 25.4 | 69.1 | 0.6 | 0.116 | 0.574 |
| 18 | 38.2 | 52.0 | 10.0 | 0.136 | 0.689 |

[a] Conversion of HMF >99% for all the reactions, Yield of 2,5-diformylfuran (DFF) almost 0 for all the reactions;
[b] $Y_{FDCA}$: Overall yield of 2,5-furandicarboxylic acid, $Y_{FFCA}$: Overall yield of 5-formylfurancarboxylic acid.

Although water was not observed to affect the conversion of substrate (which is >99% for all the reactions studied), as shown by Examples 12-18 it had a large influence on the yields of FDA and various by-products. As shown in Table 2, the yield of FDCA was high at low water concentration and reached a maximum (ca. 83%) at 10% water. Then FDCA yields decreased monotonically with further increases in water content. The severe inhibition of FDCA yield at higher water concentrations (see Examples 17 and 18) was accompanied by a significant increase in the yield of the intermediate 5-formylfurancarboxylic acid (FFCA). Water also had a marked inhibiting effect, however, on solvent and/or substrate burning, as shown by the decreased yields of gaseous by-products CO and $CO_2$, especially as the water concentration exceeded 10%.

Examples 19-24

A solution containing 1.1 mmol $Co(OAc)_2 \cdot 4H_2O$, 0.033 mmol $Mn(OAc)_2 \cdot 4H_2O$ and 1.1 mmol HBr, dissolved in 30 mL HOAc and 2 mL $H_2O$, was placed in the 50-mL titanium reactor and pressurized with 5 bar $CO_2$. The reactor was heated to the reaction temperature, followed by the addition of $CO_2$ until the reactor pressure was 30 bar and consecutive addition of 30 bar $O_2$ until the total reactor pressure was 60 bar. Following this, 5.0 mL of an HOAc solution containing dissolved 99% pure HMF (13.2 mmol) was continuously pumped into the reactor at a constant rate of 0.25 mL/min (total pumping time was therefore 20 minutes). The reaction mixture was vigorously stirred at the reaction temperature throughout the pumping duration and for another 10 minutes following addition of the HMF/HOAc solution. Then the reactor was rapidly cooled to room temperature for product separation and analysis. The results are summarized in Table 3.

TABLE 3

Effect of reaction temperature on the oxidation of HMF [a]

| Example# | Temperature (° C.) | $Y_{FDCA}$[b] (%) | $Y_{FFCA}$[b] (%) | CO/HMF (mol/mol) |
|---|---|---|---|---|
| 19 | 120 | 63.2 | 3.7 | 0.070 |
| 20 | 140 | 74.7 | 0.7 | 0.082 |
| 21 | 160 | 67.0 | 0 | 0.115 |

TABLE 3-continued

Effect of reaction temperature on the oxidation of HMF [a]

| Example# | Temperature (° C.) | $Y_{FDCA}$ [b] (%) | $Y_{FFCA}$ [b] (%) | CO/HMF (mol/mol) |
|---|---|---|---|---|
| 22 | 180 | 77.9 | 0 | 0.200 |
| 23 | 190 | 79.1 | 0 | 0.236 |
| 24 | 200 | 77.1 | 0 | 0.341 |

[a] Conversion of HMF >99% for all the reactions, Yield of 2,5-diformylfuran (DFF) almost 0 for all the reactions;
[b] $Y_{FDCA}$: Overall yield of 2,5-furandicarboxylic acid, $Y_{FFCA}$: Overall yield of 5-formylfurancarboxylic acid As shown in Table 3, the yield of FDCA was maximized in the 180-190 deg. C range. Compared with the reaction at 160 deg. C, the $O_2$ consumption profile at 180 degrees C. showed a steady consumption of $O_2$ as HMF is added, without any apparent induction period, and leveled off shortly after the HMF addition was stopped. Most of the oxygen was consumed to produce the desired product (FDCA). However, the yield of gaseous by-product CO increased at higher reaction temperatures, suggesting possible burning of the substrate, products and solvent.

Examples 25-29

A solution containing 2.2 mmol $Co(OAc)_2 \cdot 4H_2O$, 0.033 mmol $Mn(OAc)_2 \cdot 4H_2O$ and 1.1 mmol HBr, dissolved in a mixture of 30 mL HOAc and 2 mL $H_2O$, was placed in the 50-mL titanium reactor and pressurized with 3-5 bar $CO_2$. The reactor was heated to 180° C., followed by the addition of $CO_2$ to a certain pre-determined reactor pressure. Following this step, the reactor was pressurized with $O_2$ such that the ratio of the partial pressures of $CO_2$ and $O_2$ was one (i.e., $CO_2/O_2=1$). Following this step, 5.0 mL of an HOAc solution containing dissolved 99% pure HMF (13.2 mmol) was continuously pumped into the reactor at a constant rate of 0.25 mL/min (total pumping time was therefore 20 minutes). The reaction mixture was vigorously stirred at 180° C. throughout the pumping duration and for another 10 minutes following addition of the HMF/HOAc solution. Then the reactor was rapidly cooled to room temperature for product separation and analysis. The results are summarized in Table 4.

TABLE 4

Effect of reactor pressure on the oxidation of HMF [a]

| Example# | Total Pressure (bar) | $Y_{FDCA}$ [b] (%) | CO/HMF (mol/mol) |
|---|---|---|---|
| 25 | 30 | 89.6 | 0.207 |
| 26 | 34 | 86.7 | 0.226 |
| 27 | 40 | 84.5 | 0.256 |
| 28 | 50 | 82.5 | 0.268 |
| 29 | 60 | 83.3 | 0.267 |

[a] Conversion of HMF >99% for all the reactions, Yields of 5-formylfurancarboxylic acid (FFCA) and 2,5-diformylfuran (DFF) almost 0 for all the reactions;
[b] $Y_{FDCA}$: Overall yield of 2,5-furandicarboxylic acid As shown in Table 4, the yield of FDCA increased from 83% to 90% when reactor pressure was decreased from 60 bar to 30 bar. Further, the formation of gaseous by-product CO was also less favored at lower pressures.

Examples 30-35

A solution containing 1.1 mmol $Co(OAc)_2 \cdot 4H_2O$, 0.033 mmol $Mn(OAc)_2 \cdot 4H_2O$, 1.1 mmol HBr and 0.20 mmol $ZrO(OAc)_2$, dissolved in a mixture of 30 mL HOAc and 2 mL $H_2O$, was placed in the 50-mL titanium reactor and pressurized with 5 bar $CO_2$. The reactor was heated to the reaction temperature, followed by the addition of $CO_2$ until the reactor pressure was 30 bar and further addition of 30 bar $O_2$ such that the total reactor pressure was 60 bar. Following this step, 5.0 mL of an HOAc solution containing dissolved 99% pure HMF (13.2 mmol) was continuously pumped into the reactor at a constant rate of 0.25 mL/min (total pumping time was therefore 20 minutes). The reaction mixture was vigorously stirred at the reaction temperature throughout the pumping duration and for another 10 minutes following addition of the HMF/acetic acid solution. Then the reactor was rapidly cooled to room temperature for product separation and analysis. Reactions with no $ZrO(OAc)_2$ were also carried out for comparison. The results are summarized in Table 5.

TABLE 5

Effect of $ZrO(OAc)_2$ on the oxidation of HMF [a]

| Example# | $ZrO(OAc)_2$ (mmol) | Temperature (° C.) | $Y_{FDCA}$ [b] (%) | $Y_{FFCA}$ [b] (%) | CO/HMF (mol/mol) |
|---|---|---|---|---|---|
| 30 | 0 | 120 | 63.2 | 3.7 | 0.070 |
| 31 | 0.2 | 120 | 75.0 | 2.8 | 0.067 |
| 32 | 0 | 160 | 67.0 | 0 | 0.115 |
| 33 | 0.2 | 160 | 77.3 | 0 | 0.154 |
| 34 | 0 | 180 | 77.9 | 0 | 0.200 |
| 35 | 0.2 | 180 | 68.2 | 0 | 0.384 |

[a] Conversion of HMF >99% for all the reactions, Yield of 2,5-diformylfuran (DFF) almost 0 for all the reactions;
[b] $Y_{FDCA}$: Overall yield of 2,5-furandicarboxylic acid, $Y_{FFCA}$: Overall yield of 5-formylfurancarboxylic acid As shown in Table 5, the use of $ZrO(OAc)_2$ as co-catalyst increased the yield of FDCA by about 20% at 120° C. and 160° C. However, the promoting effect was diminished at 180° C., where $ZrO(OAc)_2$ facilitated considerable solvent and substrate burning, as inferred from the increased yields of gaseous product CO.

Examples 36-44

A solution of 2.2 mmol $Co(OAc)_2 \cdot 4H_2O$, 0.033 mmol $Mn(OAc)_2 \cdot 4H_2O$ and 1.1 mmol HBr, dissolved in a mixture of 30 mL HOAc and 2 mL $H_2O$, was placed in the ~50 mL titanium reactor and pressurized with 5 bar $CO_2$. The reactor was heated to 180° C., followed by the addition of $CO_2$ until the reactor pressure reached a certain value. After the introduction of an equivalent partial pressure of $O_2$ (i.e., $CO_2/O_2=1$), an HOAc solution of crude HMF was continuously pumped into the reactor at a pre-defined rate. The reaction mixture was vigorously stirred at 180° C. throughout the pumping duration (during continuous runs) and for another 10 minutes (following HMF addition during continuous runs) before the reactor was rapidly cooled to room temperature for product separation and analysis. Fixed-time batch reactions (lasting 30 min) in which all the HMF was added initially were also performed for comparison. The results are summarized in Table 6.

TABLE 6

Oxidation of Crude HMF [a]

| Example # | Crude HMF | Substrate addition mode | Substrate adding rate (mL/min) | HMF added (mmol) | Pressure (bar) | FDCA [b] produced (mmol) | FFCA [b] produced (mmol) |
|---|---|---|---|---|---|---|---|
| 36 [c] | 4956-57 | batch-wise | — | 6.74 | 60 | 0.012 | 0.056 |
| 37 | 4956-57 | batch-wise | — | 6.77 | 60 | 0.455 | 0.886 |
| 38 | 4956-57 | continuous | 0.25 | 3.15[d] | 60 | 3.22 | 0 |
| 39 | 4956-57 | continuous | 0.10 | 3.15[d] | 60 | 3.18 | 0 |
| 40 | 4956-57 | continuous | 0.25 | 1.57[d] | 60 | 1.59 | 0 |
| 41 | 5345-82 | continuous | 0.25 | 8.08[d] | 60 | 7.28 | 0 |
| 42 | 5345-82 | continuous | 0.25 | 4.04[e] | 60 | 3.97 | 0 |
| 43 | 5345-82 | continuous | 0.25 | 8.08[d] | 30 | 5.24 | 0.161 |
| 44 | 5345-82 | continuous | 0.25 | 4.04[e] | 30 | 4.23 | 0 |

[a] HMF conversion >99% for all the reactions except 90% for examples 36 and 42;
Yield of 2,5-diformylfuran (DFF) is nearly 0 for all the reactions;
[b] FDCA: 2,5-furandicarboxylic acid,
FFCA: 5-formylfurancarboxylic acid;
[c] Blank experiment with no catalyst;
[d] 5.0 mL HMF/HOAc solution added;
[e] 2.5 mL HMF/HOAc solution added As shown in Table 6, batch-wise addition of substrate afforded a very low yield of FDCA (Example 37, 0.455/6.77 =6.7%) during the oxidation of a crude HMF that contains a large amount of humins. The reaction was terminated after 10 minutes because of catalyst deactivation, signaled by formation of brown precipitates. In comparison, continuous addition of substrate managed to avoid deactivating the catalyst so rapidly and gave a much better yield of FDCA, which in some cases (Examples 38, 39, 40 and 44) exceeded 100% based on the pure HMF in the crude substrate mixture.

Example 45

To gain a better understanding of the greater than 100% yields of FDCA from crude HMF seen in Examples 38, 39, 40 and 44, an HMF dimer preparation was initially subjected to a blank experiment with no oxygen added. For this experiment, a solution containing 2.2 mmol $Co(OAc)_2 \cdot 4H_2O$, 0.11 mmol $Mn(OAc)_2 \cdot 4H_2O$ and 1.1 mmol HBr, dissolved in a mixture of 30 mL HOAc and 2 mL $H_2O$, was placed in the 50-mL titanium reactor and pressurized with 5 bar $CO_2$. The reactor was heated to 180° C., followed by the addition of $CO_2$ to a 60 bar reactor pressure. Following this step, a sample containing 0.224 mmol of the HMF dimer (5,5'-[oxy-bis(methylene)]bis-2-furfural, or OBMF) found in the crude HMF mixtures of Examples 36-44 and 0.0244 mmol of HMF was dissolved in 5.0 mL HOAc, to form a dimer feed. The dimer feed was continuously pumped into the reactor at a constant rate of 0.25 mL/min (total pumping time was therefore 20 minutes). The reaction mixture was vigorously stirred at 1200 rpm and at 180° C. throughout the pumping duration, and for another 10 minutes following addition of the dimer feed. Then the reactor was rapidly cooled to room temperature for product separation and analysis. The results of the "no oxygen" blank run were that only 6.4% (or, 0.0144 mmols) of the OBMF was converted to products in the absence of oxygen, including 0.0232 mmol AcHMF and 0.0158 mmol HMF.

Examples 46 and 47

For each of Examples 46 and 47, a solution containing 2.2 mmol $Co(OAc)_2 \cdot 4H_2O$, 0.033 mmol $Mn(OAc)_2 \cdot 4H_2O$ and 1.1 mmol HBr, dissolved in a mixture of 30 mL HOAc and 2 mL $H_2O$, was placed in the 50-mL titanium reactor and pressurized with 5 bar $CO_2$. The reactor was heated to 180° C., followed by the addition of $CO_2$ to a 60 bar reactor pressure. Following this step, a sample containing 0.224 mmols of the HMF dimer (5,5'-[oxy-bis(methylene)]bis-2-furfural, or OBMF) and 0.0244 mmol of HMF was dissolved in 5.0 mL HOAc, to form a dimer feed. After the introduction into the reactor of an equivalent partial pressure of $O_2$ (i.e., $CO_2/O_2=1$), the dimer feed was continuously pumped into the reactor at a constant rate of 0.25 mL/min (total pumping time was therefore 20 minutes). The reaction mixture was vigorously stirred at 1200 rpm and at 180° C. throughout the pumping duration, and for another 10 minutes following addition of the dimer feed. Then the reactor was rapidly cooled to room temperature for product separation and analysis. That analysis demonstrated greater than 99% conversion of both HMF and OBMF, with 0.200 and 0.207 mmol of FDCA being produced in Examples 46 and 47. Assuming the HMF in the dimer feed demonstrated 100% selectivity to the FDCA product when oxidized, and that each mole of OBMF would yield two moles of FDCA, these levels of FDCA correspond to yields of 39.1 and 40.8 percent, respectively, from OBMF.

Examples 48-52

For Examples 48-52, a 700 mL titanium spray reactor (3 inch inside diameter by 6 inches in length) equipped with a PJ® series-type, titanium fog nozzle from BETE Fog, Nozzle, Inc., Greenfield, Mass. was used to perform the oxidation of HMF to FDCA, with continuous addition of an HMF/acetic acid sprayable feed through the spray nozzle and with concurrent withdrawal of gas and liquid (with the entrained solid FDCA product) to maintain pressure control within the reactor. The PJ® series-type fog nozzles are of the impaction pin or impingement type, and according to their manufacturer produce a "high percentage" of droplets under 50 microns in size.

For each of the runs, the reactor was pre-loaded with 50 mL of acetic acid, pressurized with a 3 to 5 bars, 1:1 molar ratio mixture of carbon dioxide and oxygen and heated to the reaction temperature. Then additional carbon dioxide/oxygen was added until the reactor pressure was 15 bars. 70 mL of acetic acid was sprayed into the reactor at 35 mL/minute to establish a uniform temperature profile throughout the reactor (which was equipped with a multi-point thermocouple). Then 105 mL of an acetic acid solution containing 13.2 mmol of 99 percent pure HMF, 1.3 mmol of Co(OAc) 4H$_2$O, 1.3 mmol Mn(OAc)$_2$4H$_2$O and 3.5 mmol HBr was preheated to the reaction temperature and sprayed into the reactor at 35 mL/min, during which time a 1:1 molar ratio mixture of carbon dioxide and oxygen, also preheated to the reaction temperature, was also continuously fed into the reactor at 300 std mL/min. Both gas and liquid (with entrained solid particles) were withdrawn from the spray reactor via a line with a back pressure regulator. After a post-spray of 35 mL of acetic acid for cleaning the nozzle, the reactor was cooled to room temperature for product separation and analysis. The results were as summarized in Table 7:

TABLE 7

Continuous oxidation of HMF in the 700 mL spray reactor [a]

| | | | FDCA from separator | | FDCA in reactor | | | |
|---|---|---|---|---|---|---|---|---|
| Ex. | T (° C.) | CO$_2$/O$_2$ (mL/min) | as solid (mmol) | FFCA in solid FDCA (wt %) | in filtrate (mmol) | as solid (mmol) | in filtrate (mmol) | Y$_{FDA}$[b] (%) | Y$_{FFCA}$[b] (%) |
| 48 | 190 | 300 | 8.11 | 2.1 | 2.15 | 0 | 0.89 | 84.2 | 2.8 |
| 49 | 200 | 300 | 6.38 | 1.6 | 2.62 | 0 | 2.30 | 85.5 | 2.0 |
| 50 [c] | 200 | 300 | 7.90 | 1.9 | 1.97 | 0 | 1.47 | 84.7 | 2.6 |
| 51 | 200 | 600 | 6.70 | 2.2 | 3.39 | 0 | 0.90 | 83.4 | 2.8 |
| 52 | 220 | 300 | 2.83 | 7.9 | 3.70 | 0 | 3.20 | 72.3 | 8.6 |

[a] Conversion of HMF >99% for all the reactions;
[b] Overall yield based on the products from both separator and reactor;
[c] Example 50 shows good reproducibility with Example 49.

As shown in Table 7, the continuous oxidation of HMF at 200° C. and 15 bars affords about an 85% yield of FDCA and about 2% FFCA (Examples 49 and 50), with the majority of products collected from the separator during the 3 min spray process. Both of the reactor temperature and pressure were very well controlled. The reaction becomes less productive with further increase of the temperature to 220° C., giving 72.3% yield of FDCA and 8.6% yield of FFCA (Example 52). As well, the concentration of FFCA in solid FDCA product is increased from 1.6% (Example 50, 200° C.) to 7.9% (Example 52, 220° C.). Higher temperatures favor solvent and substrate burning, which decrease the oxygen available for FDCA formation. The FDCA yield and solid product purity do not benefit by doubling the feed rate of the gas mixture (compare Example 50 and Example 51). The increased oxygen availability might be offset by the decrease of residence time in the gas phase at higher gas flow rate.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. Unless otherwise indicated, all references or publications recited herein are incorporated herein by specific reference.

The invention claimed is:

1. A process for carrying out an oxidation on a sprayable feed including a crude dehydration product of natural hexose as a furanic substrate to be oxidized and a catalytically effective combination of cobalt, manganese, and bromide components for catalyzing the oxidation of the furanic substrate, comprising the steps of:

acid dehydrating a natural hexose to provide a crude dehydration product as a furanic substrate to be oxidized;

directly incorporating the crude dehydration product into the sprayable feed;

spraying the feed into a reactor vessel;

supplying oxygen or an oxygen-containing gas as an oxidant to the reactor vessel;

reacting the furanic substrate and the oxidant in the presence of the cobalt, manganese and bromide components to form 2,5-furandicarboxylic acid; and managing the exothermic temperature rise due to the reaction, through a selection and control of the operating pressure within the reactor vessel.

2. A process according to claim 1, wherein the operating pressure within the reactor vessel is selected and controlled so that the boiling point of at least one liquid present in the reactor vessel as the oxidation reaction is underway is from 10 to 30 degrees Celsius greater than the temperature at which the oxidation reaction is begun.

3. A process according to claim 2, wherein the process is carried out as a continuous process, and wherein the operating pressure control is accomplished at least in part by continuously withdrawing materials from the reactor vessel.

4. A process according to claim 2, wherein the feed contains one or more of 5-hydroxymethylfurfural and its ester and ether derivatives as a furanic substrate or substrates to be oxidized to provide 2,5-furandicarboxylic acid, the feed includes acetic acid, and 2,5-furandicarboxylic acid precipitates out as an oxidation product and is recovered from the reactor vessel as a substantially pure solid.

5. A process according to claim 4, wherein the exothermic temperature rise is managed through using, at least in part, the latent heat of evaporation of acetic acid to remove heat released through the oxidation reaction, such that a temperature of between 160 degrees Celsius and 200 degrees Celsius is maintained in the reactor vessel during the course of the oxidation reaction.

6. A process according to claim 5, wherein the operating pressure does not exceed 40 bars.

7. A process according to claim 4, wherein acetic acid vapor is provided to the reactor vessel prior to the feed stream's being sprayed into the reactor.

8. A process according to claim 7, wherein the reactor vessel is substantially saturated with acetic acid vapor, as the feed begins to be sprayed into the reactor vessel.

9. A process according to claim 8, wherein the reactor vessel is kept substantially saturated with acetic acid vapor at least in part by maintaining liquid acetic acid within the reactor vessel.

10. A process according to claim 9, wherein the amount of liquid acetic acid present is maintained substantially constant by withdrawing liquid acetic acid from the reactor vessel at substantially the same volumetric rate as acetic acid is sprayed into the reactor vessel via the feed.

11. A process according to claim 10, wherein solid oxidation product is removed with the withdrawn liquid acetic acid, then is separated from the liquid acetic acid with at least a portion of the liquid acetic acid then being recycled for use in additional feed for the process.

12. A process according to claim 1, wherein the feed includes one or more of 5-hydroxymethylfurfural and the ester and ether derivatives of 5-hydroxymethylfurfural and wherein the Co, Mn and Br components collectively comprise from 0.4 to 2.0 weight percent of the feed.

13. A process according to claim 1, wherein fructose, glucose or a combination thereof are acid-dehydrated to provide the crude dehydration product.

14. A process according to claim 1, wherein the sprayable feed is preheated to the reaction temperature before being sprayed into the reactor vessel.

15. A process for making 2,5-furandicarboxylic acid from fructose, glucose or a combination of fructose and glucose, comprising:
   acid dehydrating the fructose, glucose or combination thereof to provide a dehydration product comprising 5-hydroxymethylfurfural, or acid dehydrating the fructose, glucose or combination thereof in the presence of an alcohol to provide a dehydration product comprising an ether of 5-hydroxymethylfurfural, or acid dehydrating the fructose, glucose or combination thereof in the presence of a carboxylic acid to provide a dehydration product comprising an ester of 5-hydroxymethylfurfural;
   directly solubilizing the dehydration product from the acid dehydration step and a catalytically effective combination of cobalt, manganese, and bromide components in a liquid solvent, to form a sprayable feed composition;
   spraying the sprayable feed composition into a reactor vessel as a mist;
   supplying oxygen or an oxygen-containing gas to the reactor vessel;
   reacting the oxygen and the 5-hydroxymethylfurfural or ether or ester thereof in the dehydration product to form 2,5-furandicarboxylic acid; and
   recovering 2,5-furandicarboxylic acid from the reactor vessel.

16. A process according to claim 15, wherein the liquid solvent is an aqueous acetic acid solution, and the 2,5-furandicarboxylic acid is recovered as a substantially pure solid.

* * * * *